(12) United States Patent
Amon (10) Patent No.: US 12,279,793 B2
(45) Date of Patent: Apr. 22, 2025

(54) CANNULA DEVICE

(71) Applicant: Fresenius Kabi Deutschland GmbH, Bad Homburg (DE)

(72) Inventor: Barbara Amon, Oberursel (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 498 days.

(21) Appl. No.: 17/637,886

(22) PCT Filed: Oct. 9, 2020

(86) PCT No.: PCT/EP2020/078386
§ 371 (c)(1),
(2) Date: Feb. 24, 2022

(87) PCT Pub. No.: WO2021/074023
PCT Pub. Date: Apr. 22, 2021

(65) Prior Publication Data
US 2022/0280192 A1 Sep. 8, 2022

(30) Foreign Application Priority Data
Oct. 16, 2019 (EP) .................................... 19203483

(51) Int. Cl.
*A61B 17/34* (2006.01)
(52) U.S. Cl.
CPC ...... *A61B 17/3494* (2013.01); *A61B 17/3415* (2013.01); *A61B 17/3496* (2013.01); *A61B 2017/3445* (2013.01); *A61B 2017/347* (2013.01)
(58) Field of Classification Search
CPC . A61B 17/3494; A61B 17/3496; A61B 17/34; A61B 17/3401; A61B 17/3403;
(Continued)

(56) References Cited

U.S. PATENT DOCUMENTS 5,275,583 A * 1/1994 Crainich ............ A61B 17/3496
604/164.12
5,290,243 A * 3/1994 Chodorow ......... A61B 17/3496
604/164.12
(Continued)

FOREIGN PATENT DOCUMENTS

CN 108601609 A 9/2018
DE 4103977 A1 * 8/1992
(Continued)

OTHER PUBLICATIONS

International Search Report and Written Opinion, counterpart International App. No. PCT/EP2020/078386 (Nov. 13, 2020) (8 pages).
(Continued)

*Primary Examiner* — Katherine M Shi
(74) *Attorney, Agent, or Firm* — Cook Alex Ltd.

(57) ABSTRACT

A cannula device (1) comprises a housing (11), a cannula (10) arranged on the housing (11), and a puncture device (17) which, in a use state, is arranged on the housing (11) and comprises a puncture trocar (18) received in the cannula (10). The puncture trocar (18) is displaceable with respect to the cannula (10) and comprises a trocar tip (180) which, by displacing the puncture trocar (18) with respect to the cannula (10) in a puncturing direction (P), is movable to protrude from the cannula (10) in said puncturing direction (P), wherein the puncture device (17) is removable from the housing (11) in a removal direction (A) opposite the puncturing direction (P). A protection element (15) is received in the housing (11) and comprises a connection portion (150) arranged on the puncture trocar (18) and at least one shielding leg (152, 153) pivotably connected to the connection portion (150), wherein the puncture trocar (18) is configured to carry the protection element (15) along when the puncture trocar (18) is removed from the housing (11) in said removal direction (A), the at least one shielding leg
(Continued)

(152, 153) being configured to be pivotably moved with respect to the connection portion (150) to approach the trocar tip (180) when the protection element (15) is carried along by the puncture trocar (18).

11 Claims, 12 Drawing Sheets

(58) Field of Classification Search
CPC .... A61B 2017/3405; A61B 2017/3407; A61B 2017/3409; A61B 17/3415; A61B 17/3417; A61B 17/3421; A61B 2017/3445; A61B 17/3423; A61B 2017/3425; A61B 2017/3427; A61B 2017/347; A61B 17/3474; A61M 25/0618; A61M 25/06; A61M 25/0612; A61M 25/0631; A61M 5/1626; A61M 5/321; A61M 5/3213
See application file for complete search history.

(56) References Cited

U.S. PATENT DOCUMENTS

| | | | |
|---|---|---|---|
| 5,538,509 A | | 7/1996 | Dunlap et al. |
| 5,810,863 A | * | 9/1998 | Wolf .................. A61B 17/3496 606/167 |
| 6,117,108 A | * | 9/2000 | Woehr .............. A61M 25/0625 604/110 |
| 6,203,527 B1 | | 3/2001 | Zadini et al. |
| 6,595,954 B1 | * | 7/2003 | Luther .............. A61M 25/0618 604/110 |
| 2004/0078003 A1 | | 4/2004 | Smith et al. |
| 2005/0182363 A1 | * | 8/2005 | Kulli .................. A61M 25/0618 604/110 |
| 2008/0249478 A1 | * | 10/2008 | Ishikura ............ A61M 25/0618 604/198 |
| 2009/0281499 A1 | * | 11/2009 | Harding ............ A61M 25/0618 604/164.08 |
| 2010/0241087 A1 | * | 9/2010 | Moulton ........... A61M 25/0618 604/263 |
| 2011/0301551 A1 | | 12/2011 | Koehler et al. |
| 2018/0021057 A1 | | 1/2018 | Mohajer-Shojaee |
| 2018/0256209 A1 | * | 9/2018 | Muse .................. A61M 5/3273 |

FOREIGN PATENT DOCUMENTS

| | | | | |
|---|---|---|---|---|
| EP | 2774596 | | 9/2014 | |
| WO | WO-2011011263 A2 | * | 1/2011 | ............. A61M 5/158 |
| WO | WO-2015067106 A1 | * | 5/2015 | ............. A61M 5/158 |
| WO | WO-2016199597 A1 | * | 12/2016 | ............. A61B 10/02 |

OTHER PUBLICATIONS

Office Action and Search Report (with translation), counterpart Chinese App. No. 202080072920.8 (Dec. 28, 2024) (19 pages).

* cited by examiner

CANNULA DEVICE

The present application is a U.S. National Stage of PCT International Patent Application No. PCT/EP2020/078386, filed Oct. 9, 2020, which claims priority to EP Application No. 19203483.3, filed Oct. 16, 2019, both of which are hereby incorporated herein by reference.

The invention relates to a cannula device according to the preamble of claim 1.

A cannula device of this kind serves to provide an access to a human body cavity, such as a visceral cavity (for example the gastro intestinal tract). A cannula device of this kind may be used for example for an enteral feeding of a patient and, for this, may be percutaneously inserted into and placed inside a patient's body cavity.

A cannula device of this kind comprises a housing, a cannula arranged on the housing, and a puncture device which, in a use state, is arranged on the housing. The puncture device comprises a puncture trocar received in the cannula, the puncture trocar being displaceable with respect to the cannula and comprising a trocar/trocartip which, by displacing the puncture trocar with respect to the cannula in a puncturing direction, is movable to protrude from the cannula in said puncturing direction. The puncture device is removable from the housing in a removal direction opposite the puncturing direction.

By means of such a cannula device an access may be provided on a body cavity, allowing the placement of a tubing within the body cavity to allow for example for a long-term enteral feeding of the patient. For providing the access, herein, the patient's skin is punctured by means of the puncture device and, together with the puncture device, the cannula device is inserted to access the body cavity of interest, for example the gastro intestinal tract of the patient. After inserting the cannula device into the body cavity, the puncture device may be removed from the housing and the cannula, and a thread may be inserted through the cannula to enter the body cavity. The thread may be grabbed by means of a suitable grabbing device inserted into the body cavity for example through the patient's esophagus, upon which a tubing may be connected to the thread and may be moved into the body cavity by pulling the thread through the cannula of the cannula device. The tubing may in this way be placed within the access formed by the cannula device and may remain in the access after removing the cannula device.

During the use of the cannula device, the cannula of the cannula device shall be placed within the body cavity of interest, upon which the puncture device including the puncture trocar shall be removed from the housing and the cannula received thereon. Such step of removing the puncture device may present a safety risk in that a user, such as a physician or a nurse, may be hurt by the puncture trocar, involving a risk of injury as well as a risk of infection for the user.

Cannula devices are known from the art that use protecting members which, upon removal of a puncture device from a housing of the cannula device, are carried along by a puncture trocar to cover a trocar tip of the puncture trocar. Cannula devices of this kind are for example known from EP 2 774 596 A1 and US 2004/078003 A1.

It is an object of the instant invention to provide a cannula device which allows for a protection of a user in particular during removal of the puncture device from the housing, wherein the cannula device shall be reliable in use and easy and cost-efficient in its manufacturing.

This object is achieved by means of a cannula device comprising the features of claim 1.

Accordingly, the cannula device comprises a protection element received in the housing and comprising a connection portion arranged on the puncture trocar and at least one shielding leg pivotably connected to the connection portion, wherein the puncture trocar is configured to carry the protection element along when the puncture trocar is removed from the housing in said removal direction, the at least one shielding leg being configured to be pivotably moved with respect to the connection portion to approach the trocar tip when the protection element is carried along by the puncture trocar.

When the puncture device is removed from the housing, it automatically carries a protection element along which serves to cover and shield the trocar tip of the puncture trocar such that a user is protected from injury upon removal of the puncture device from the housing. Because the protection element is carried along by the puncture trocar when removing the puncture device from the housing and the cannula, a user does not come into contact with the trocar tip of the puncture trocar and hence may not be hurt by the puncture trocar.

The protection element herein comprises a connector portion and at least one shielding leg pivotably connected to the connection portion. The connection portion serves to interact with the puncture trocar when removing the puncture trocar from the housing, wherein during the removal the at least one shielding leg is moved pivotably with respect to the connection portion to approach the trocar tip. Hence, when removing the puncture device from the housing, the at least one shielding leg is moved to cover the trocar tip, such that the trocar tip is shielded towards the outside and may not hurt a user after removing the puncture device from the housing.

The protection element may be manufactured in an easy and cost efficient manner. For example, the protection element may be an integral piece made from a plastics material, the at least one shielding leg being integrally formed with the connection portion and being elastically movable with respect to the connection portion upon removing the puncture device from the housing.

Once the at least one shielding leg is caused to be approached towards the trocar tip, the protection element is further carried along with the puncture device and is removed from the housing together with the puncture device, such that in a removed state the protection element is arranged on the trocar tip and covers and shields the trocar tip for providing a protection at the trocar or trocar tip.

In one embodiment, the at least one shielding leg, in the use state of the puncture device, assumes a first pivot position. In the use state of the puncture device, the protection element is received within the housing, the at least one shielding leg herein being in a position in which it diverts from the puncture trocar. When removing the puncture device from the housing and when, accordingly, the protection element is carried along by the puncture trocar, the at least one shielding leg is moved from the first pivot position to a second pivot position in which the at least one shielding leg is approached towards the trocar tip. In the second pivot position the at least one shielding leg hence assumes a position in which it is approached towards the trocar tip and may cover and shield the trocar tip towards the outside, such that the trocar tip upon removal from the housing may not come into contact with a user and hence may not cause an injury for the user.

In one embodiment, the at least one shielding leg comprises a half shell portion which (in cross section) extends along an arc about the removal direction and, in the second pivot position, receives the trocar tip within. The at least one shielding leg hence has the shape of a curved shell formed to cover and shield the trocar tip such that, in the second pivot position, the at least one shielding leg extends at least partially about the trocar tip and hence provides for a protection by preventing an immediate contact of the trocar tip with a user.

In one embodiment, the at least one shielding leg, in the second pivot position, axially extends beyond the trocar tip. The trocar tip hence does not axially protrude from the protection element and the at least one shielding leg formed thereon, but, in contrast, the at least one shielding leg protrudes beyond the trocar tip and may reach radially inward to reach around the immediate tip of the puncture trocar to provide for an axial cover of the trocar tip.

In one embodiment, the at least one shielding leg comprises a locking element for locking the at least one shielding leg in the second pivot position. The locking element may for example be formed to provide for a positive locking, the positive locking being established automatically upon moving the at least one shielding leg towards the second pivot position. Due to the locking, the at least one shielding leg is safely held in the second pivot position such that the protection element may not easily be removed from the trocar tip and hence provides for a reliable protection at the trocar tip.

In one embodiment, the protection element comprises two shielding legs, which each are pivotably connected to the connection portion. The two shielding legs herein may be arranged diametrically opposite to one another at the connection portion and, in a first pivot position, may each be arranged to divert from the puncture trocar. Upon removing the puncture trocar from the housing, the shielding legs are pivoted towards their second pivot position, wherein each shielding leg may comprise a locking element, the locking elements of the shielding elements being configured to interlock with each other when being approached towards one another. The locking elements may for example be configured to establish a positive locking connection, the locking elements coming into engagement with one another when the shielding legs are pivoted to approach each other, such that the shielding legs are locked with respect to each other and receive the trocar tip within for providing a protection at the trocar tip.

In one embodiment, the connection portion is shaped as a ring forming an opening through which the puncture trocar extends. The connection portion is hence placed on the puncture trocar and interacts with the puncture trocar such that the connection portion is carried along when the puncture trocar is removed from the cannula device when removing the puncture device from the housing.

In one embodiment, the housing comprises at least one guide section, wherein the connection portion is received on the at least one guide section. The at least one guide section herein is configured to act onto the at least one shielding leg when the protection element is carried along by the puncture trocar during removal of the puncture device from the housing. Hence, by carrying the protection element along the at least one shielding leg of the protection element is caused to interact with one or multiple guide sections formed on the housing, the guide sections causing the at least one shielding leg to be pivoted from the first pivot position towards the second pivot position and hence to assume a position in which the trocar tip is covered by the at least one shielding leg.

In one embodiment, the at least one shielding leg comprises a run-up slope to interact with the at least one guide section formed on the housing. When carrying the protection element along, the shielding leg comes into contact by means of its run-up slope with an associated guide section of the housing such that the shielding leg is pivoted with respect to the connection portion of the protection element and hence is approached towards the trocar tip to cover and shield the trocar tip.

In one embodiment, the puncture trocar comprises a carrier element configured to act onto the connection portion for carrying the protection element along during removal of the puncture device from the housing. The carrier element may for example be formed by a protrusion formed near the trocar tip on the puncture trocar. By means of the carrier element the puncture trocar acts onto the connection portion of the protection element such that the connection portion and hence the protection element is moved together with the puncture trocar, the at least one shielding leg in this way being caused to interact with the housing in order to pivot the at least one shielding leg from its first pivot position towards the second pivot position to approach the trocar tip and hence to cover and shield the trocar tip.

In one embodiment, the cannula device comprises an actuation member which, in a movable fashion, is arranged on the housing. The actuation member may be actuated to allow a displacing of the puncture trocar with respect to the cannula.

Herein, the actuation element, in one embodiment, may comprise at least one detent element which, in a locked state, engages with the puncture device and hence blocks the puncture device with respect to the housing. In a non-actuated state of the actuation element the puncture device hence is fixedly arrested with respect to the housing such that the puncture trocar may not be moved within the cannula. For allowing a moving of the puncture device, the actuation member may be actuated such that the at least one detent element is released from the puncture device and the puncture device may be axially moved, along the puncturing direction, to cause the puncture trocar to axially protrude from the cannula in order to percutaneously puncture a patient's skin and to insert the cannula device into a body cavity of interest of the patient.

Likewise, the actuation member may be actuated for removing the puncture device from the housing, causing the protection element to be carried along for covering and shielding the trocar tip.

The idea of the invention shall subsequently be described in more detail with respect to the embodiment shown in the figures. Herein.

Figure 1:
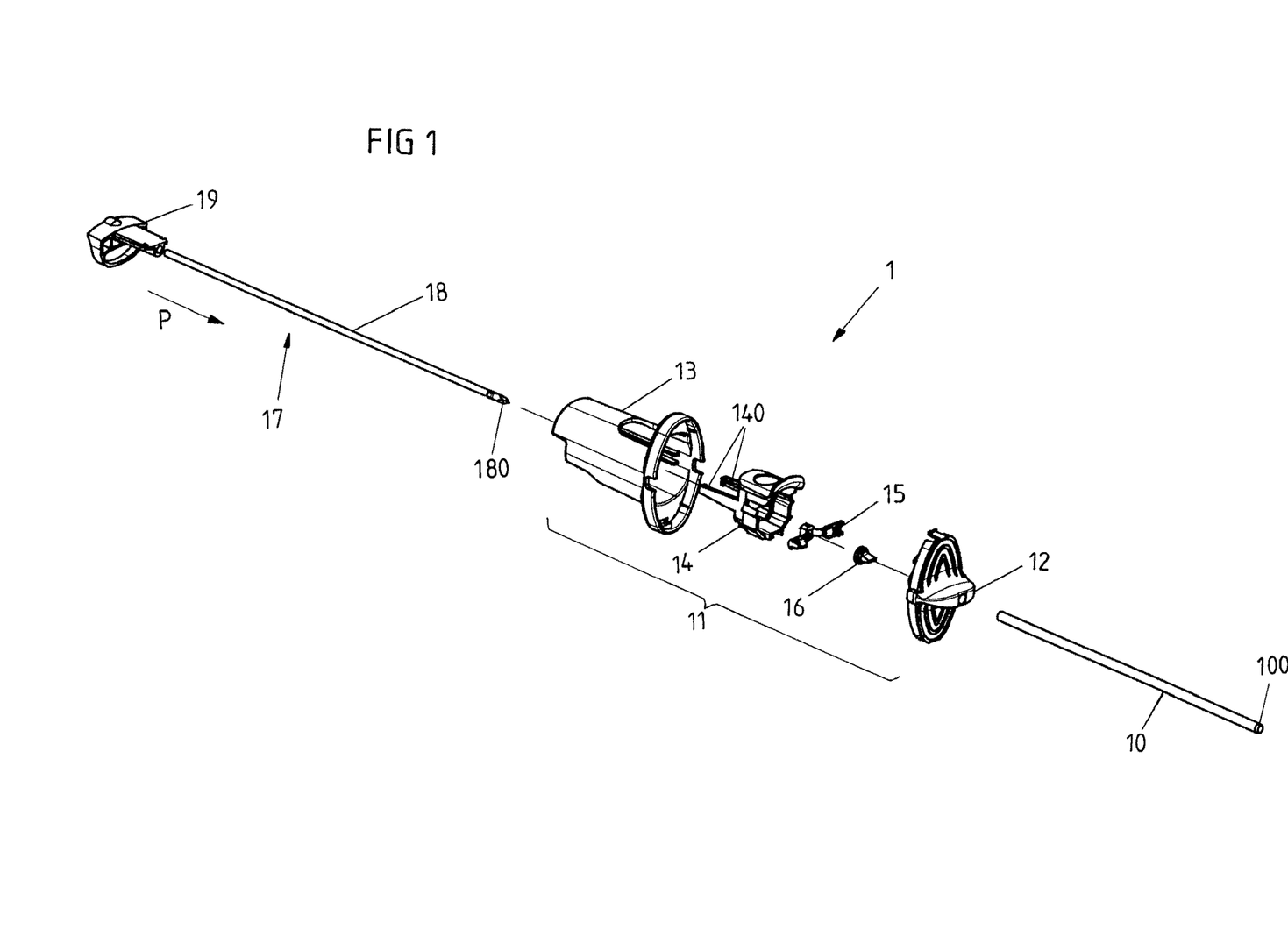
FIG. 1 shows an explosive view of an embodiment of a cannula device.
Figure 2:
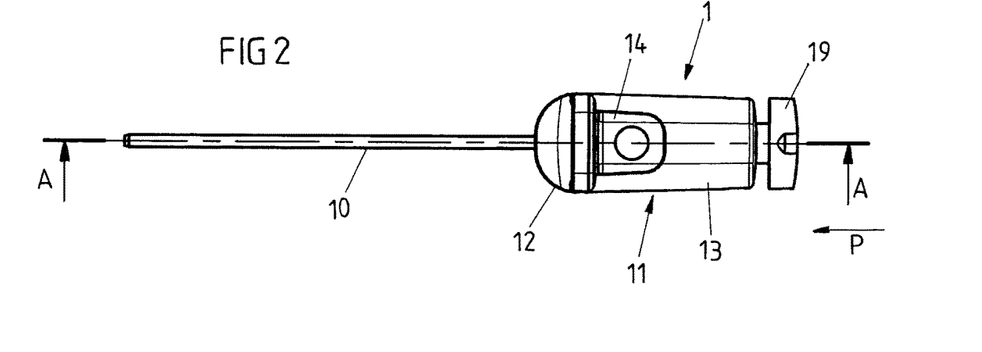
FIG. 2 shows a top view of the cannula device.
Figure 3:
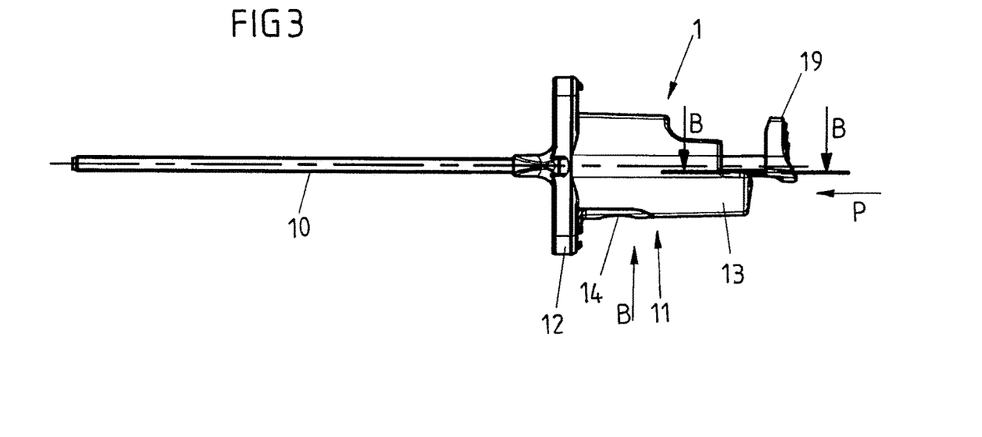
FIG. 3 shows a side view of the cannula device.

FIGS. 1 to 3 show an embodiment of a cannula device 1 comprising a housing 11 and a cannula 10 received thereon. The housing 11 comprises housing parts 12, 13, which are connected to each other and receive a puncture device 17. The puncture device 17, with a puncture trocar 18, is placed in an initial use state within the cannula 10 and comprises a head 19 arranged at a proximal end of the housing 11.

Figure 4:
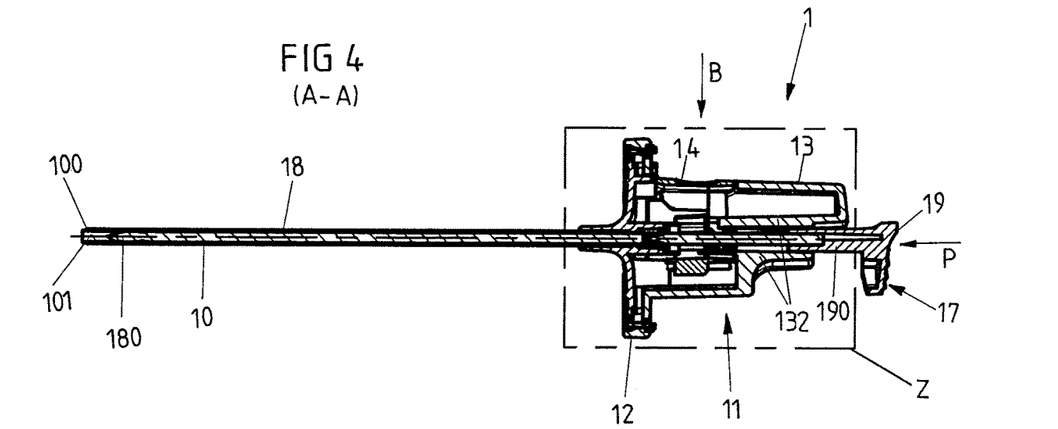
FIG. 4 shows a cross-sectional view along line A-A as illustrated in FIG. 2.

The cannula 10 forms, at a distal end, a cannula tip 100 by means of which the cannula 10 may be inserted percutaneously into a patient's skin in order to provide a percutaneous access to a body cavity within the patient. As visible from the sectional view of FIG. 4, the puncture trocar 18 of the puncture device 17 is received within an inner channel 101 of the cannula 10 such that, in the initial use state, the puncture trocar 18 with a trocar tip 180 is arranged within the cannula 10 and does not axially protrude from the cannula 10.

Figure 5:
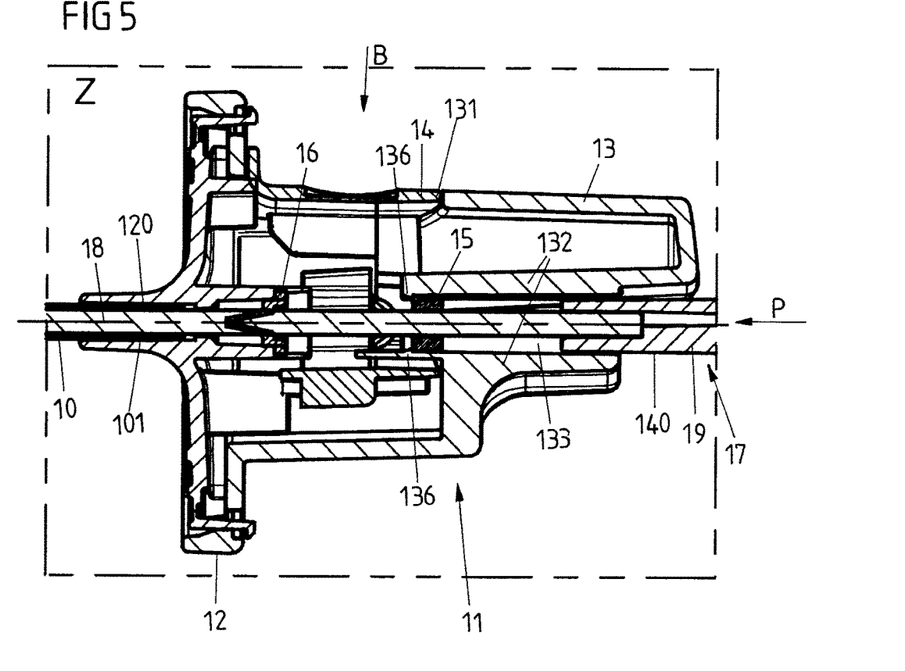
FIG. 5 shows a portion Z as indicated in FIG. 4 in an enlarged fashion.

The head 19 of the puncture device 17 is arranged on the housing part 13 of the housing 11, whereas the cannula 10 is received within a receptacle 120 formed on the housing parts 12, as this is visible from the enlarged sectional view of FIG. 5. The puncture trocar 18 is connected to a shaft 190 of the head 19, the shaft 190 being guided in between guide walls 132 formed within the housing part 13. The puncture trocar 18 extends from the shaft 190 through an opening in the housing part 12 into the cannula 10 and hence is slidably received within the cannula 10.

Within the housing 11, further an actuation member 14 is received which serves to lock the puncture device 17, in the initial use state, with respect to the housing 11 such that the puncture device 17 is held with respect to the housing 11 and may not axially be moved with respect to the housing 11. The puncture trocar 18 hence is locked with respect to the housing 11 and may not involuntarily be moved with respect to the cannula 10 such that the puncture trocar 18 cannot, with its trocar tip 180, by accident protrude from the cannula tip 100.

Referring now to FIGS. 5 to 8, the actuation member 14 is received within an opening 131 of the housing part 13 of the housing 11 and is placed within an inner space 130 of the housing 11. The actuation member 14 can be actuated in an actuation direction B to push the actuation member 14 into the housing 13 in order to unlock the puncture device 17 such that the puncture device 17 becomes axially movable with respect to the housing 11.

Figure 6:
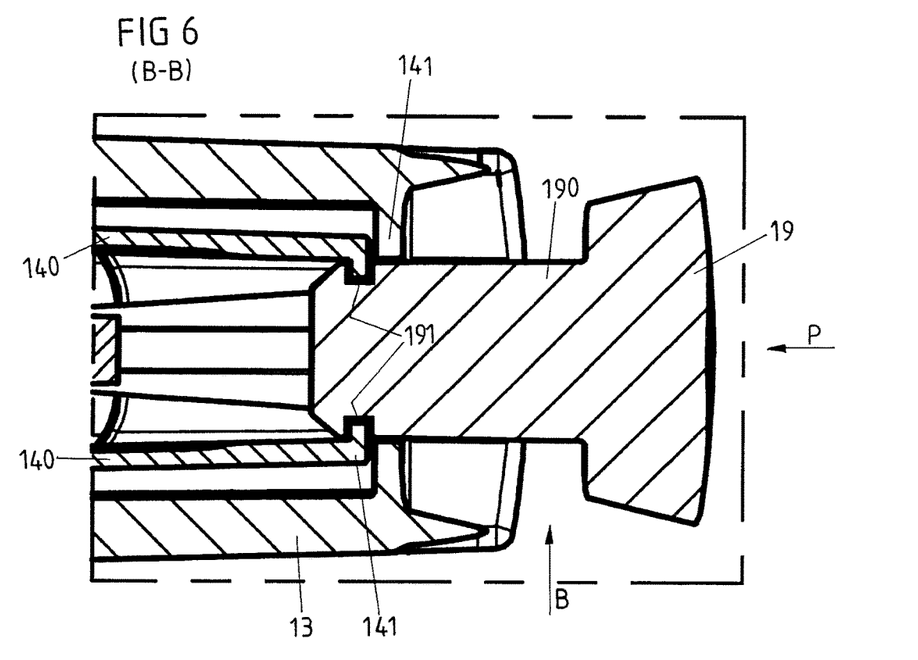
FIG. 6 shows an enlarged cross-sectional view along line B-B as illustrated in FIG. 3.
Figure 7:
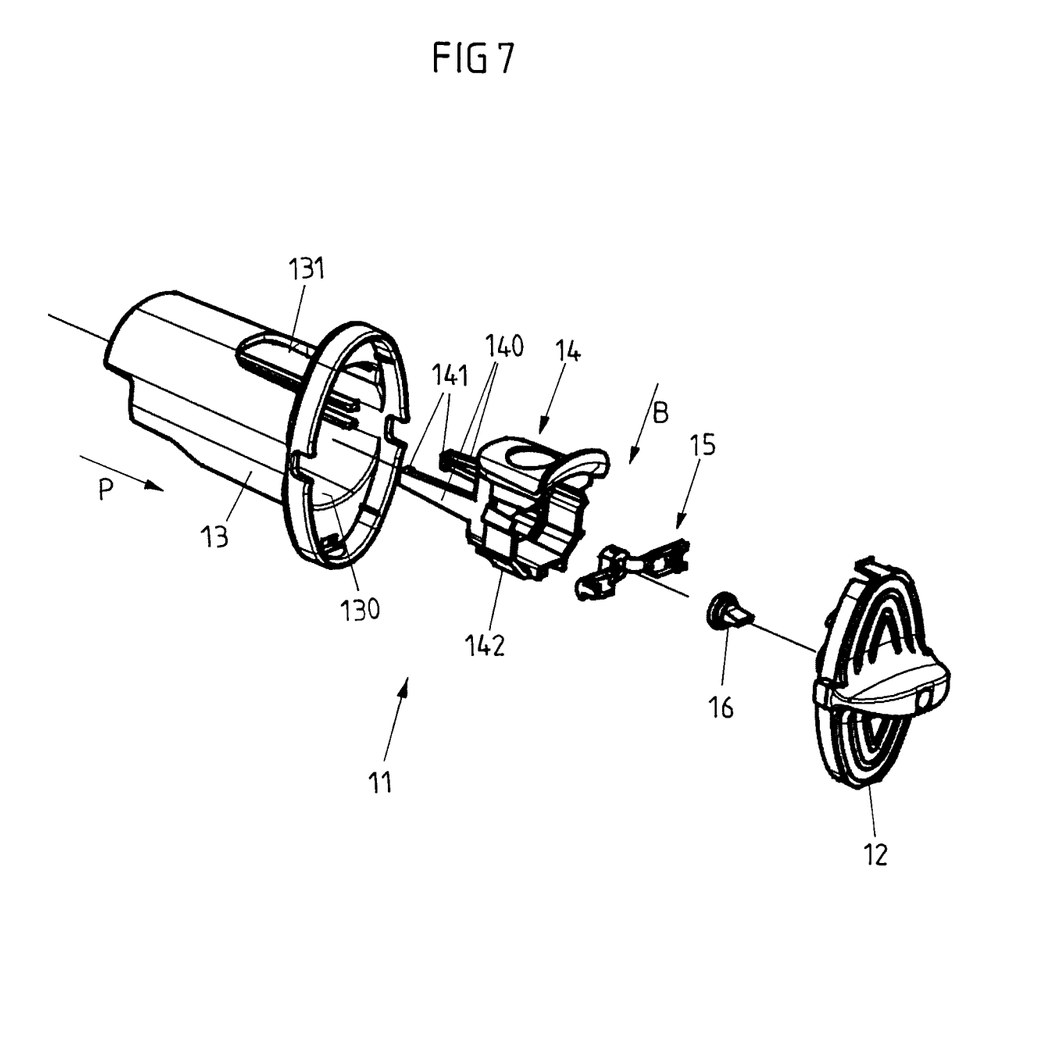
FIG. 7 shows an enlarged view of a housing of the cannula device, including an actuation member and a protection element.
Figure 8:
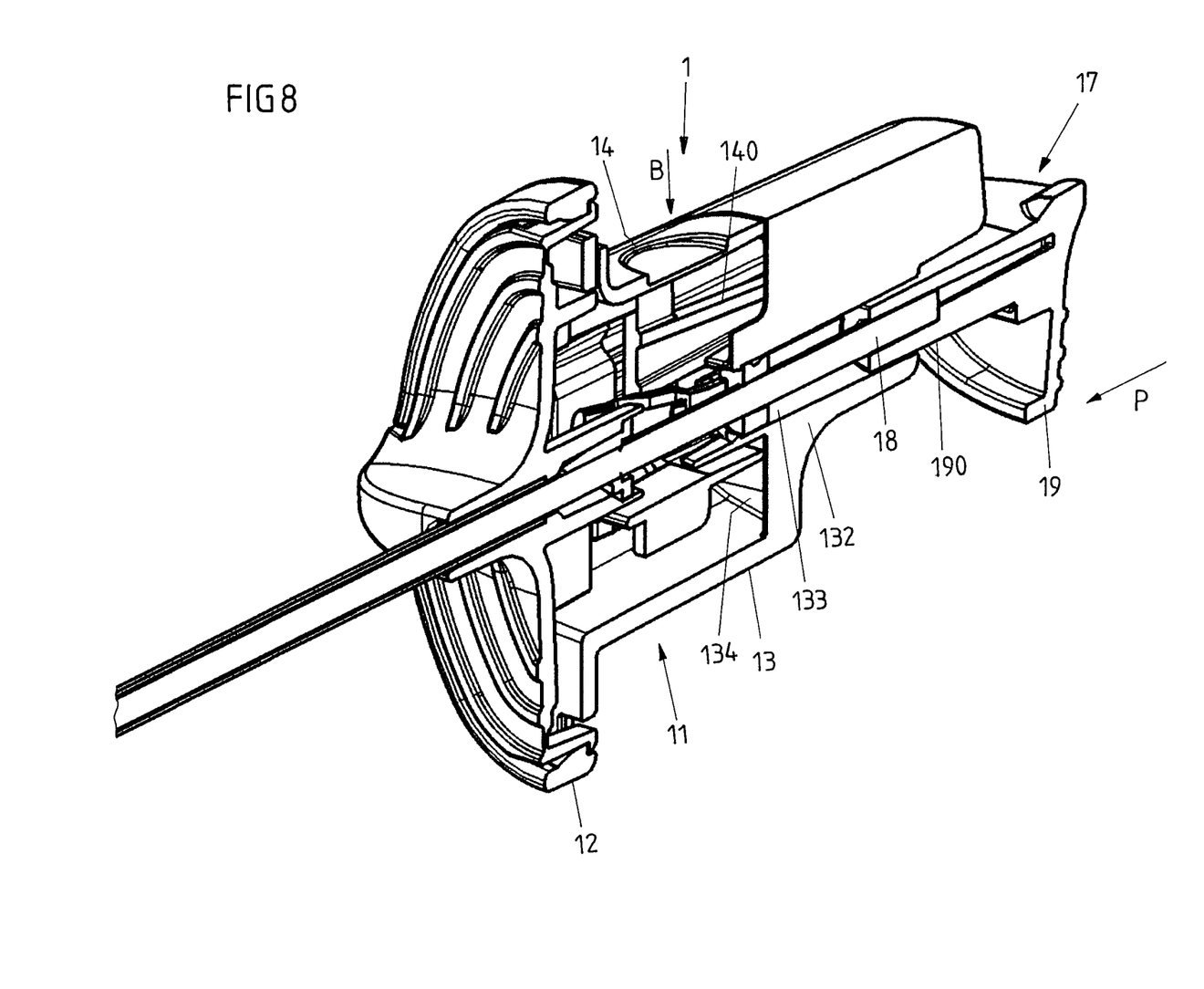
FIG. 8 shows a sectional view of the housing with a puncture device received therein.

As visible from FIG. 7 in view of FIGS. 6 and 8, the actuation member 14 comprises detent elements 140 in the shape of arms protruding from a body portion 142, each detent element 140 carrying an engagement nose 141 at a far end with respect to the body portion 142. In the initial use state, as visible from FIG. 6, the engagement noses 141 engage with locking receptacles 191 formed on the shaft 190 of the head 19 of the puncture device 17, such that the puncture device 17 is axially locked with respect to the housing 11 by means of the actuation member 14.

By actuating the actuation member 14 the detent elements 140 are moved transversely to the shaft 190 of the head 19 of the puncture device 17, such that the engagement noses 141 are disengaged from the locking receptacles 191 formed on the shaft 190. The puncture device 17 hence becomes free to move with respect to the housing 11 along a puncture direction P, such that a user may push on the head 19 in order to move the puncture trocar 18 with respect to the cannula 10 to cause the trocar tip 180 of the puncture trocar 18 to axially protrude from the cannula tip 100 of the cannula 10 for puncturing a patient's skin.

Figure 9:
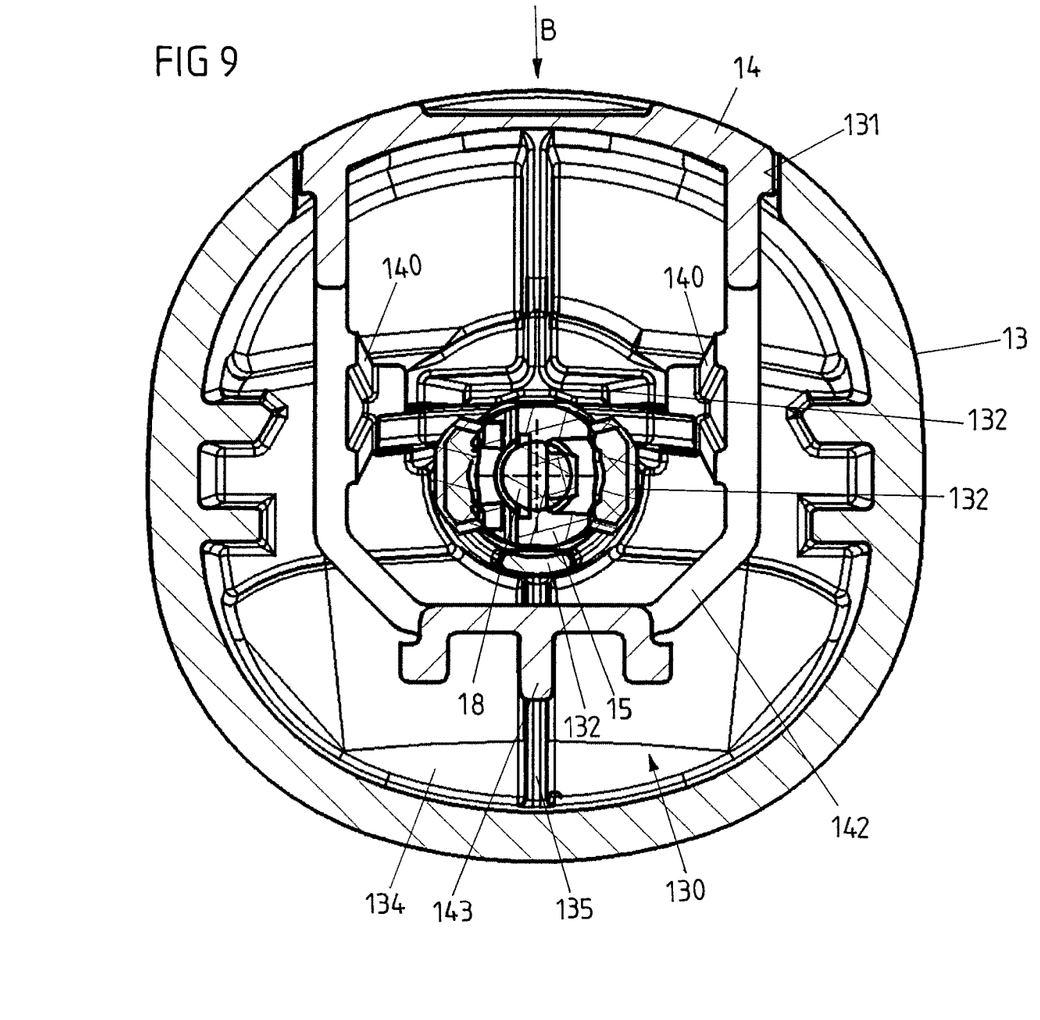
FIG. 9 shows a cross-sectional view of the housing with the actuation member placed therein.

Referring now to FIG. 9, the actuation member 14 is guided on the housing part 13 of the housing 11 along the actuation direction B—which is arranged at a perpendicular angle with respect to the puncturing P—in that guide elements 143 are formed on the body portion 142 of the actuation member 14, the guide elements 143 being guided along a longitudinal guide 135 formed on a rear wall 134 of the housing part 13. Due to the longitudinal guiding a tilting of the actuation member 14 during actuation is prevented, such that the actuation member 14 may reliably be actuated to disengage the detent elements 140 from the shaft 190 and to hence unlock the puncture device 17.

Referring now again to FIG. 7, in addition a protection element 15 and an anti-air-ventilation valve 16 (for preventing air to exit from a body cavity during operation) are received within the housing 11.

As visible from FIG. 7 in view of FIG. 5, the puncture trocar 18 of the puncture device 17 extends through the anti-air-ventilation valve 16 to seal a transition in between the housing part 12 and the puncture trocar 18 in a fluid-tight manner such that air may not exit through the housing 11 and the cannula 10.

The protection element 15 serves to provide a protection when removing the puncture device 17 from the housing 11.

Figure 10:
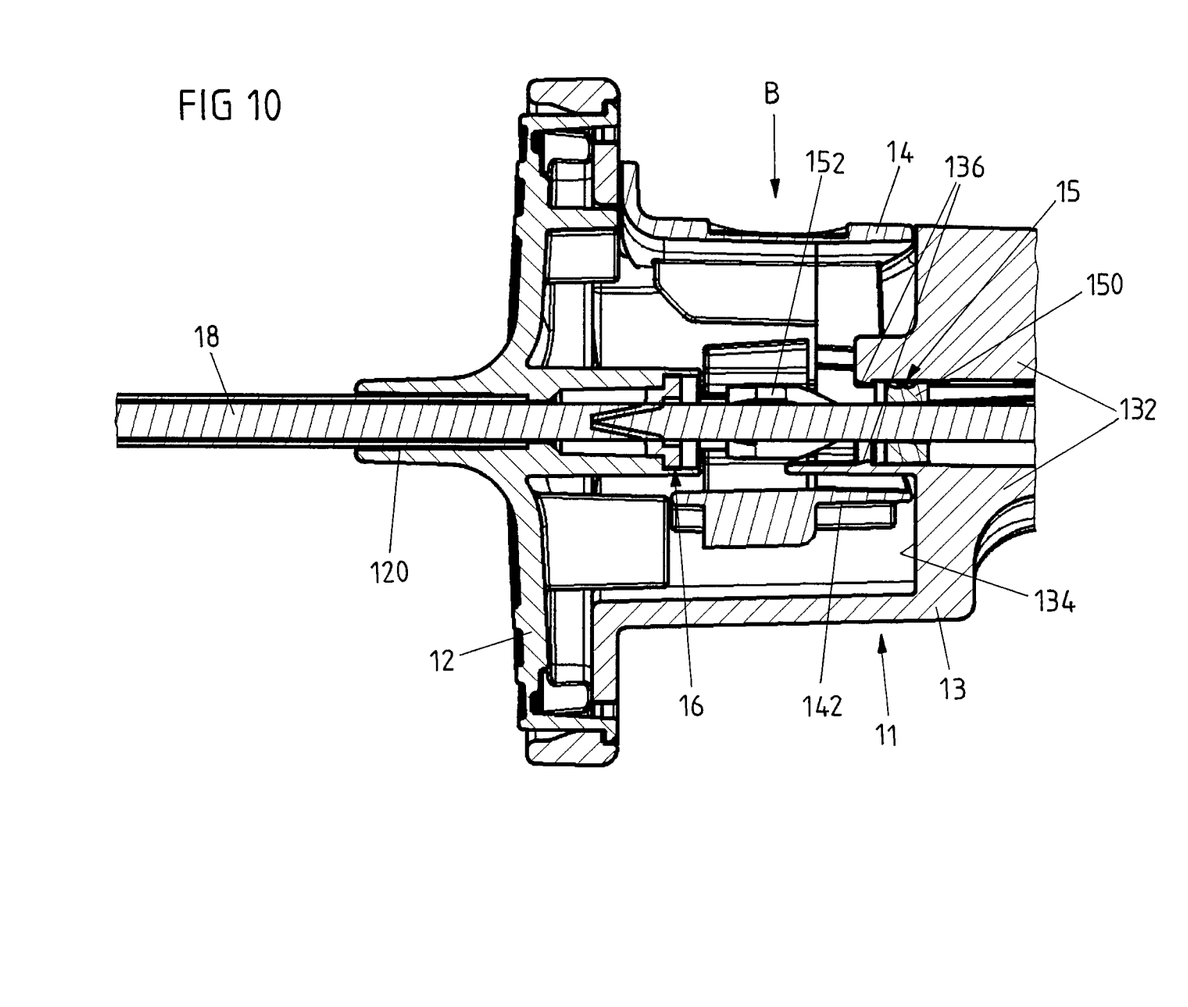
FIG. 10 shows another sectional view of the housing.
Figure 11:
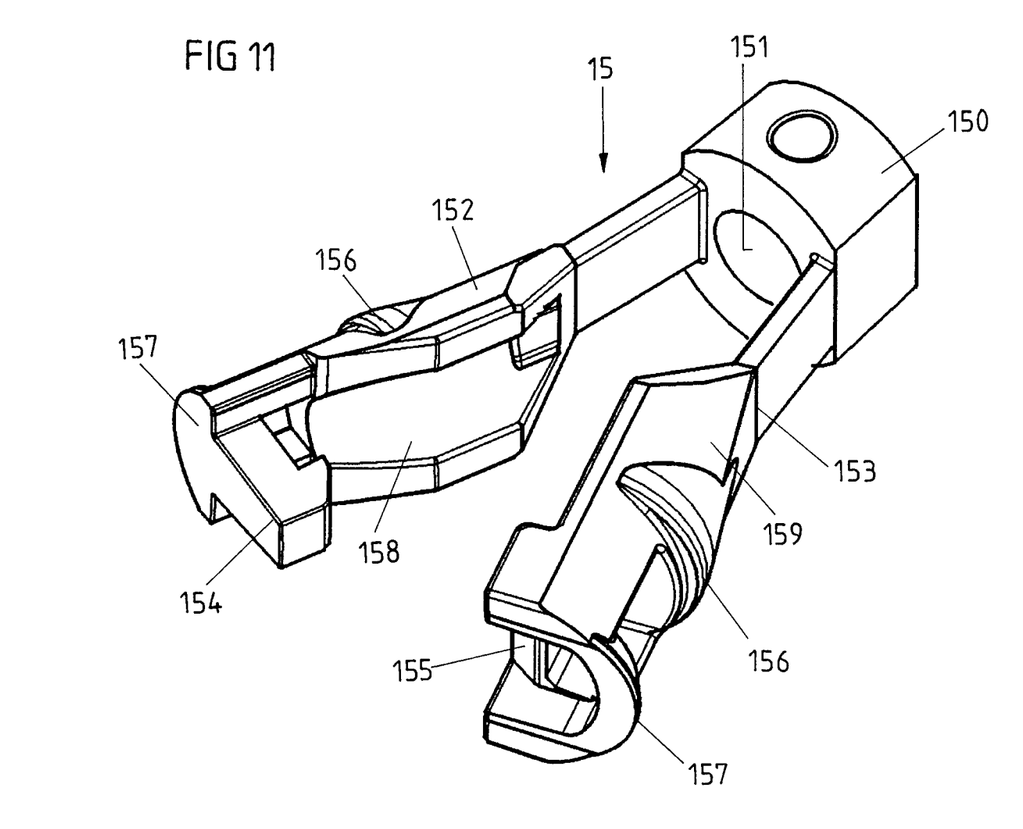
FIG. 11 shows a view of the protection element.
Figure 12:
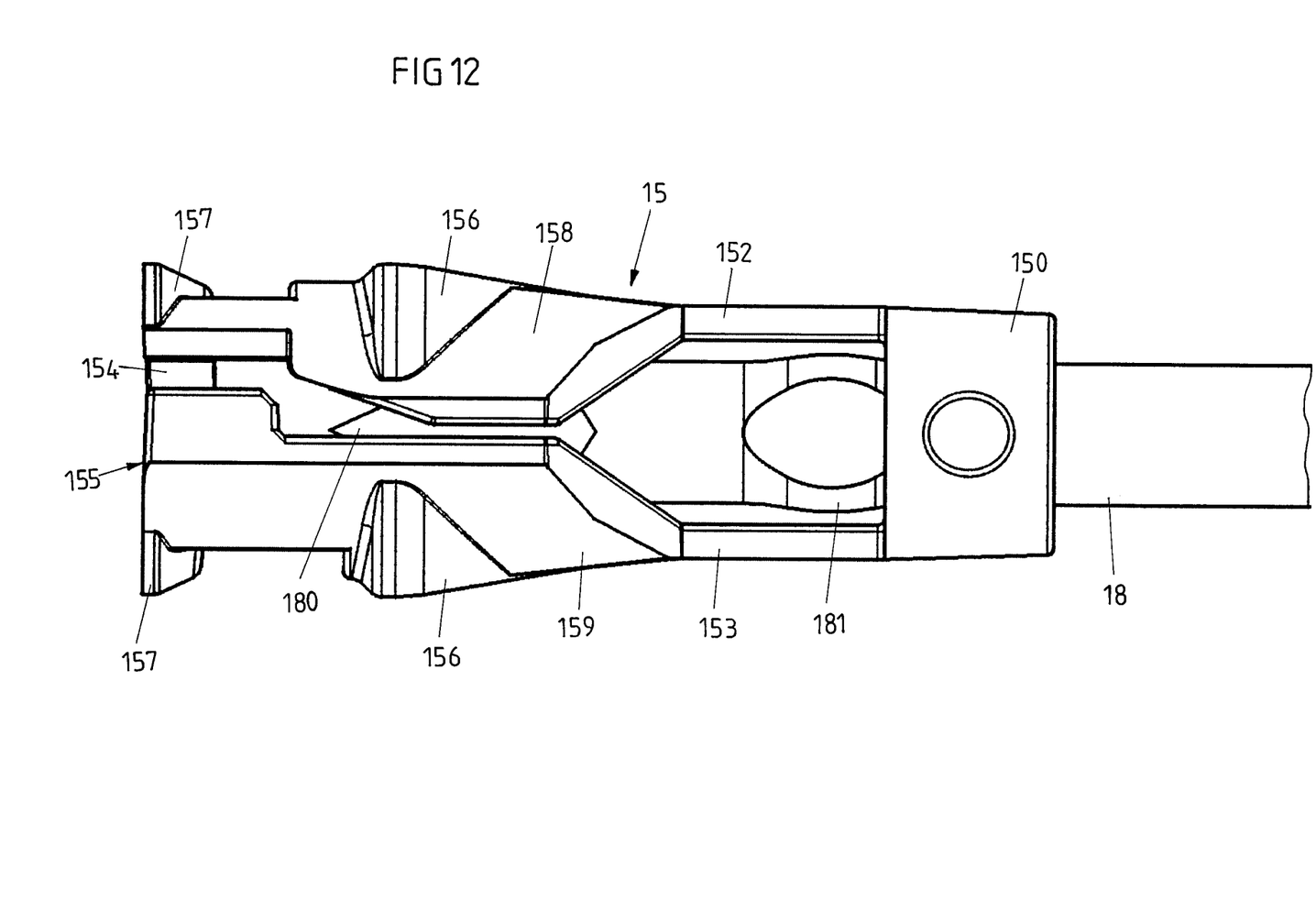
FIG. 12 shows a view of the protection element arranged on the trocar tip of a puncture trocar of the puncture device.

Referring now to FIGS. 10 to 12, the protection element 15 comprises a connection portion 150 in the shape of a ring in which an opening 151 is formed. The connection portion 150 is arranged on the puncture trocar 18 such that the puncture trocar 18 extends through the opening 151 formed within the connection portion 150.

Herein, as visible from FIG. 10, the connection portion 150 is received in between the guide walls 132 formed within the housing part 13 of the housing 11, such that the protection element 15 is movable with respect to the housing 11 along a defined guide channel 133 formed within the housing 11.

The puncture trocar 18 may slidably be moved with respect to the protection element 15. The connection portion 150 in turn may slidably move within the guide channel 133 formed in between the guide walls 132, stop portions 136 formed at the ends of the guide walls 132 however preventing that the connection portion 150 in the puncturing direction P may be moved out of the guide channel 133 formed in between the guide walls 132.

As visible from FIGS. 11 and 12, the protection element 15, in the shown embodiment, comprises two shielding legs 152, 153. The shielding legs 152, 153 herein are connected to the connection portion 150 such that they elastically may be deformed with respect to the connection portion 150 for pivoting the shielding legs 152, 153 with respect to the connection portion 150.

The protection element 15 in the shown embodiment is integrally formed in one piece for example from a plastics material.

In a relaxed state, the shielding legs 152, 153 assume a position in which they are arranged at an angle with respect to each other and hence divert from the connection portion 150 such that the shielding legs 152, 153 assume a V-shape, as visible from FIG. 11. The shielding legs 152, 153 however may be pivoted with respect to the connection portion 150 in order to approach each other such that the shielding legs 152, 153 may engage with each other to receive the trocar tip 180 of the puncture trocar 18 within, as visible from FIG. 12.

Each shielding leg 152, 153 comprises a half shell portion 158, 159 having an arc shape—when viewed in a cross-section perpendicular to the puncturing direction P—such that the shielding legs 152, 153 together form a receptacle for the trocar tip 180.

At a far end with respect to the connection portion 150 each shielding leg 152, 153 comprises a locking element 154, 155, one locking element 154 being formed as a hook, whereas the other locking element 155 is formed as a locking web, the locking elements 154, 155 being configured to interact with each other to establish a positive locking connection for interlocking the shielding legs 152, 153 with respect to each other.

On the outside of each half shell portion 158, 159 a run-up slope 156 is formed, which serves to interact with an associated guide wall 132 formed within the housing 13. In addition, another run-up slope in the shape of wedge is formed at the outside edge at a far end of each shielding leg 152, 153.

Figure 13A:
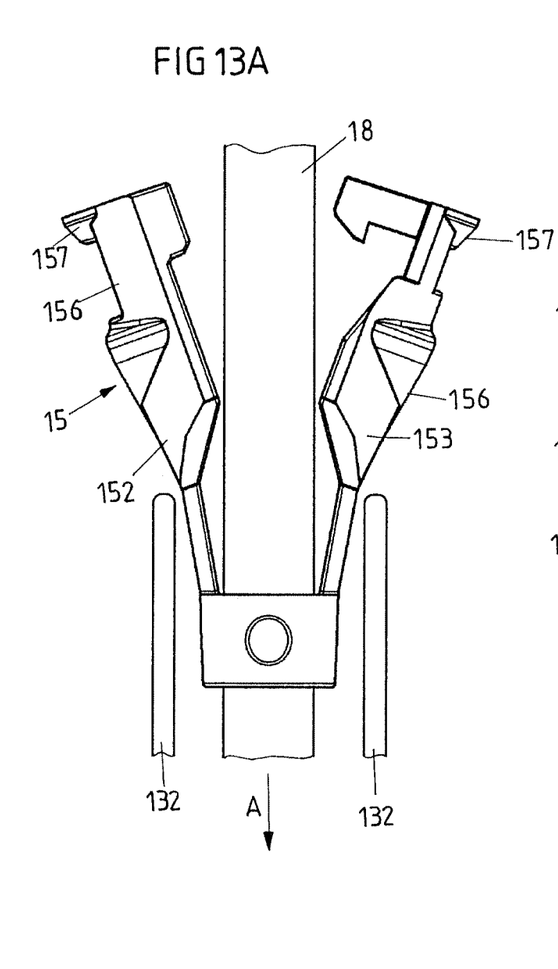
FIG. 13A shows a view of the protection element, prior to pivoting shielding legs to cover the trocar tip.
Figure 13B:
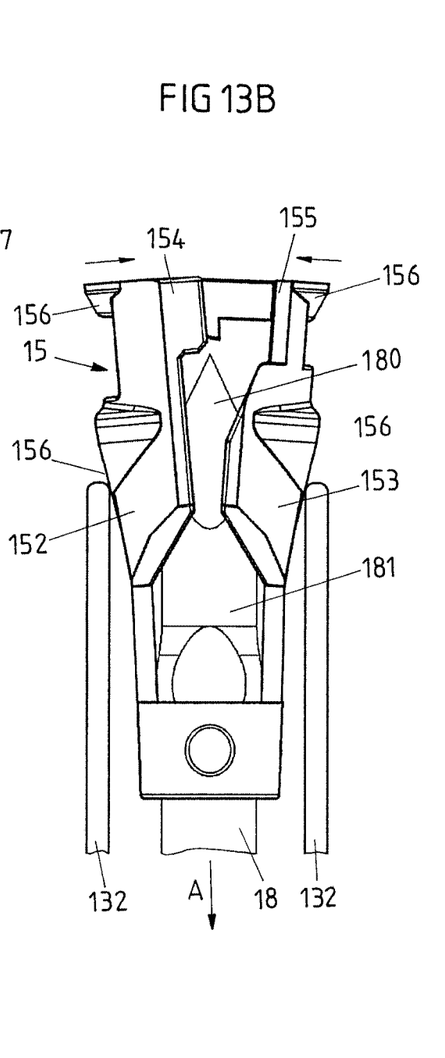
FIG. 13B shows a view of the protection element while pivoting the shielding legs to approach one another.
Figure 13C:
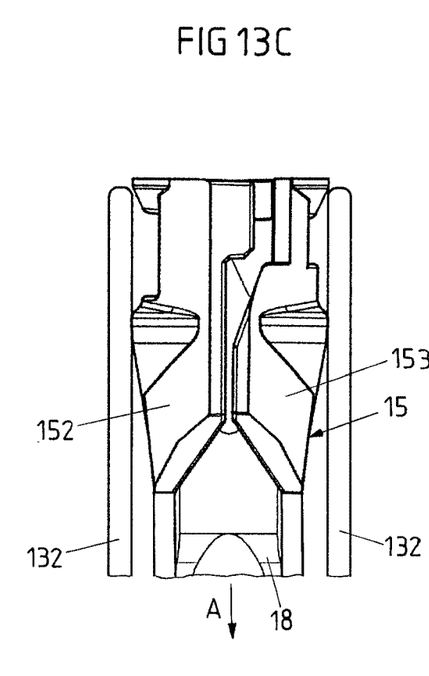
FIG. 13C shows the protection element, with the shielding legs approached towards and locked with respect to one another.

Referring now to FIGS. 13A to 13C, the run-up slopes 156 at the outside of the half shell portions 158, 159 of the shielding legs 152, 153 come into contact with front edges of the guide walls 132 formed within the housing part 13 of the housing 11 when the puncture device 17 is removed from the housing 11 in a removal direction A opposite the puncturing direction P, causing the shielding legs 152, 153 to be pivoted inwards to approach each other.

Herein, when removing the puncture device 17 from the housing 11, a carrier element 181 in the shape of a protrusion formed on the puncture trocar 18 in the vicinity of the trocar tip 18 interacts with the connection portion 150 of the protection element 15 extending circumferentially around the puncture trocar 18, such that the protection element 15 is carried along in the removal direction A with the puncture device 17. Because the protection element 15 is carried along, the shielding legs 152, 153 are pulled into the guide channel 133 formed in between the guide walls 132, and hence are approached towards one another and are locked with respect to each other by means of the locking elements 154, 155 to cover and shield the trocar tip 180.

FIGS. 14A to 14E illustrate a potential mode of use of the cannula device 1.

Figure 14A:
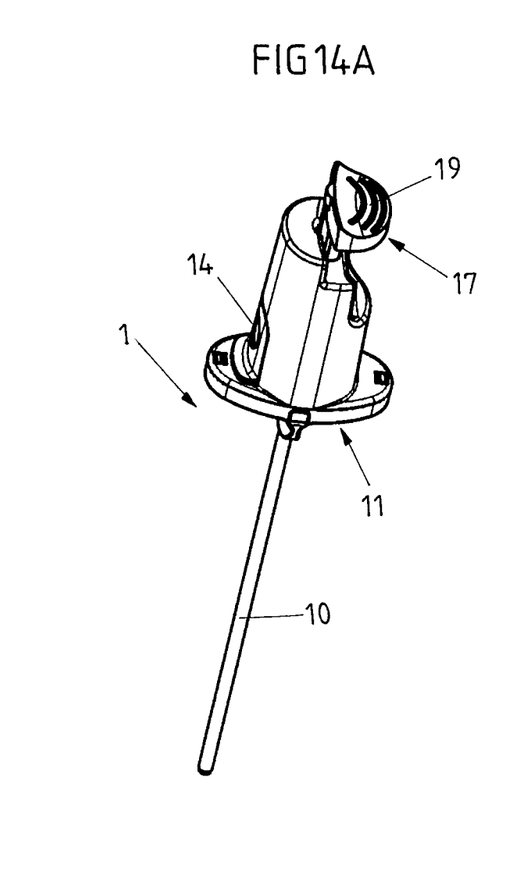
FIG. 14A shows the cannula device prior to accessing a body cavity.

In an initial use state, illustrated in FIG. 14A and corresponding for example to a delivery state of the cannula device 1, the actuation member 14 is non-actuated and hence locks the puncture device 17 with respect to the housing 11. The puncture trocar 18 is received in the cannula 10, without however protruding from the distal end of the cannula 10.

Figure 14B:
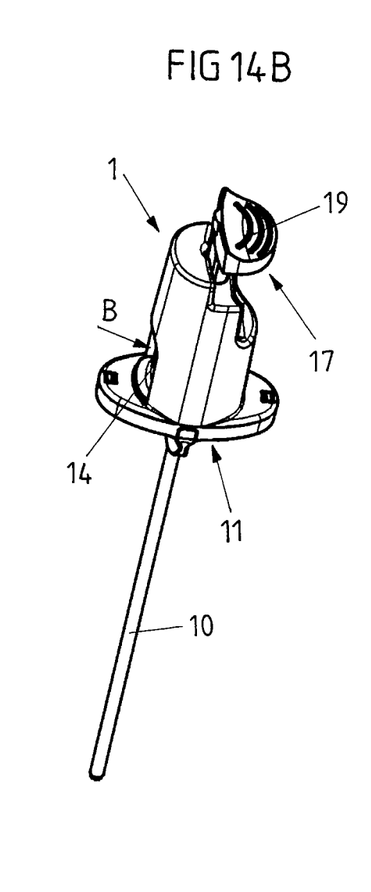
FIG. 14B shows the cannula device when actuating the actuation member for activating the puncture device.
Figure 14C:
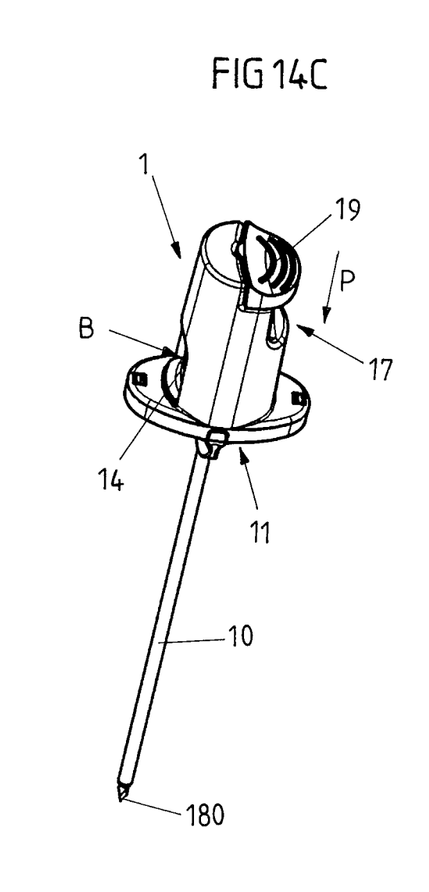
FIG. 14C shows the cannula device, with the puncture device being moved to puncture a patient's skin.

By actuating the actuation member 14 in the actuation direction B, as shown in FIG. 14B, the puncture device 17 is unlocked and hence is free to move with respect to the housing 11. A user may hence press on the head 19 of the puncture device 17 and in this way may move the puncture device 17 in the puncturing direction P, such that the puncture trocar 18 axially slides within the cannula 10 and with its trocar tip 180 is caused to protrude from the distal end of the cannula 10, as shown in FIG. 14C. In this state the cannula device 1 may be used to percutaneously puncture a patient's skin in order to insert the cannula 10 into a body cavity of the patient.

Figure 14D:
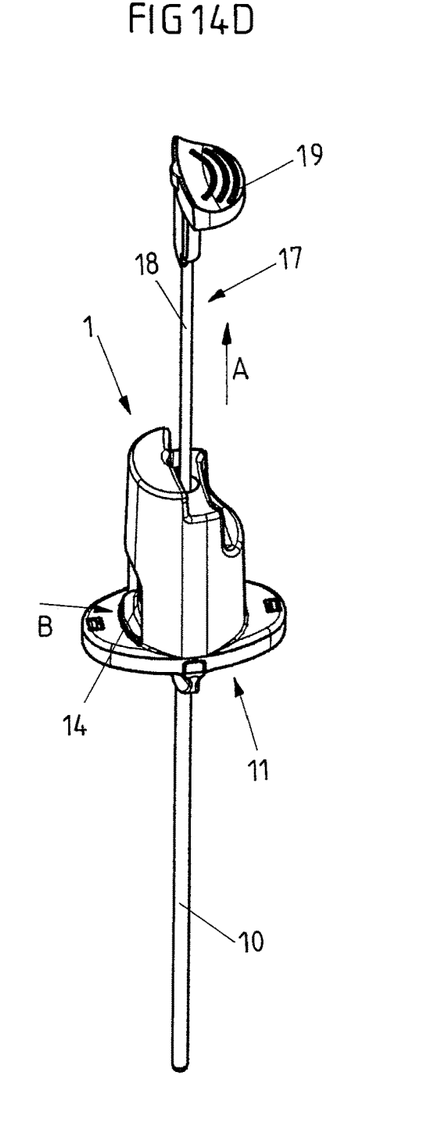
FIG. 14D shows the cannula device, during removal of the puncture device.
Figure 14E:
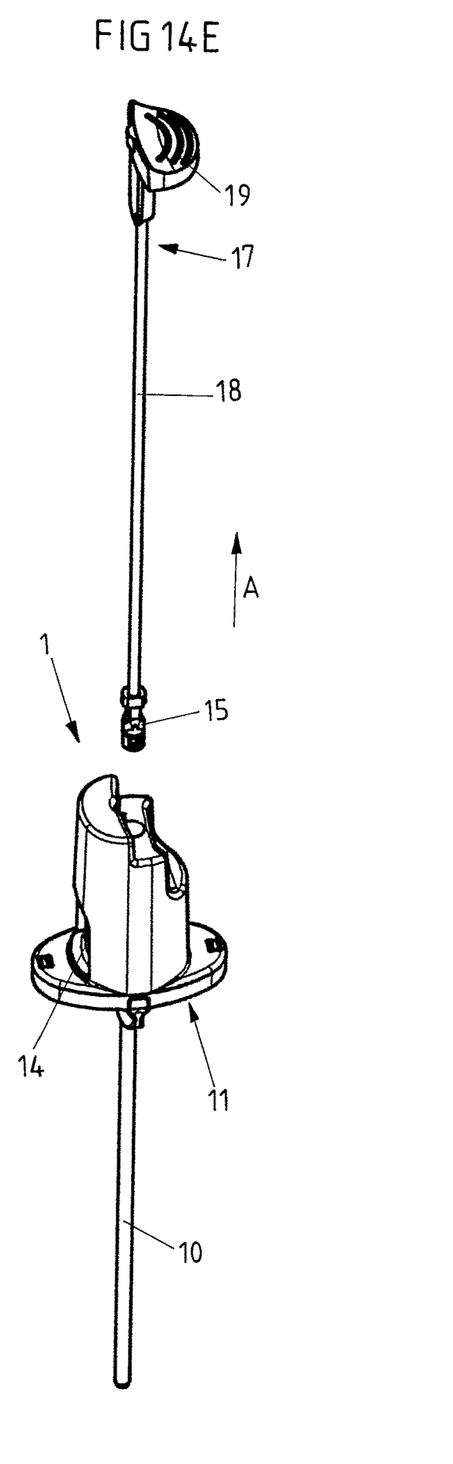
FIG. 14E shows the cannula device, with the puncture device removed.

Upon insertion into the body cavity, the puncture device 17 shall be removed from the housing 11 such that, for example, a thread may be inserted into the cannula 10 for placing a tubing in the access formed by the cannula device 1. For this, the actuation member 14 is held unlocked, and the puncture device 17 is pulled out of the housing 11 in the removal direction A opposite the puncturing direction P, as shown in FIGS. 14D and 14E. During the removal, the puncture trocar 18 with its carrier element 181 formed in the vicinity of the trocar tip 180 interacts with the protection element 15 in the housing 11 and carries the protection element 15 along, the protection element 15 coming to rest at the trocar tip 180 and hence covering and shielding the trocar tip 180 once the puncture device 17 is removed from the housing 11.

Because the protection element 15 automatically is carried along and covers the trocar 180, a reliable protection and shielding is provided, substantially reducing a risk for an injury and potential infection of a user.

The actuation member 14 may be spring-elastically biased with respect to the housing 11 using a spring element, such as a pressure spring, towards of the non-actuated position.

The idea of the invention is not limited to the embodiments described herein, but may be implemented in another fashion.

The housing as well as the cannula and the puncture trocar may have a different shape than in the embodiment shown in the figures.

A cannula device of the kind described herein may for example be used to provide an access for the long-term enteral feeding of a patient but may also be used in a different medical context to provide an access to a body cavity of a patient.

LIST OF REFERENCE NUMERALS

1 Puncture Cannula device
10 Cannula
100 Cannula tip (distal end)
101 Channel
11 Housing
12 Housing part
120 Receptacle
13 Housing part
130 Space
131 Opening
132 Guide wall
133 Guide channel
134 Rear wall
135 Longitudinal guide (web)
136 Stop portions
14 Actuation member 140 Detent elements (locking arms)
141 Engagement nose
142 Body portion
143 Guide elements
15 Protection element
150 Connection portion (ring element)
151 Opening
152, 153 Shielding leg
154, 155 Locking element
156, 157 Run-up slope
158, 159 Half shell portion
16 Anti-air-ventilation valve
17 Puncture device
18 Puncture trocar
180 Trocar tip
181 Carrier element (protrusion)
19 Head
190 Shaft
191 Locking receptacle
A Removal direction
B Actuation direction
P Puncturing direction

The invention claimed is:

1. A cannula device, comprising:
a housing,
a cannula arranged on the housing, and
a puncture device which, in a use state, is arranged on the housing and comprises a puncture trocar received in the cannula, the puncture trocar being displaceable with respect to the cannula and comprising a trocar tip which, by displacing the puncture trocar with respect to the cannula in a puncturing direction, is movable to protrude from the cannula in said puncturing direction, wherein the puncture device is removable from the housing in a removal direction opposite the puncturing direction, and
a protection element received in the housing and comprising a connection portion arranged on the puncture trocar and two shielding legs pivotably connected to the connection portion, wherein the puncture trocar is configured to carry the protection element along when the puncture trocar is removed from the housing in said removal direction, the two shielding legs being configured to be pivotably moved with respect to the connection portion to approach the trocar tip when the protection element is carried along by the puncture trocar,
wherein each of the two shielding legs, in the use state of the puncture device, assumes a first pivot position arranged to divert from the puncture trocar and, when the protection element is carried along by the puncture trocar, is moved from the first pivot position to a second pivot position in which the each of the two shielding legs is approached towards the trocar tip,
wherein one of the two shielding legs comprises a first locking element for locking the two shielding legs in the second pivot position, and
wherein at least one of the two shielding legs comprises a half shell portion which extends along an arc about the removal direction and, in the second pivot position, receives the trocar tip within.

2. The cannula device according to claim 1, wherein the at least one of the two shielding legs comprising the half shell portion, in the second pivot position, axially extends beyond the trocar tip.

3. The cannula device according to claim 1, wherein the other one of the two shielding legs comprises a second locking element, the first and second locking elements of the shielding legs being configured to interlock with each other when being approached towards each other.

4. The cannula device according to claim 1, wherein the connection portion is shaped as a ring forming an opening through which the puncture trocar extends.

5. The cannula device according claim 1, wherein the housing comprises at least one guide section, wherein the connection portion is received on the at least one guide section, the at least one guide section being configured to act onto the two shielding legs when the protection element is carried along by the puncture trocar during removal of the puncture device from the housing.

6. The cannula device according to claim 5, wherein each of the two shielding legs comprises a run-up slope to interact with the at least one guide section.

7. The cannula device according to claim 1, wherein the puncture trocar comprises a carrier element configured to act onto the connection portion for carrying the protection element along during removal of the puncture device from the housing.

8. The cannula device according to claim 1, further comprising an actuation member arranged on the housing, the actuation member being actuatable to allow displacement of the puncture trocar with respect to the cannula.

9. The cannula device according to claim 8, wherein the actuation member comprises at least one detent element which, in a locked state, engages with the puncture device for locking the puncture device with respect to the housing.

10. The cannula device according to claim 9, wherein by actuating the actuation member the at least one detent element is releasable from the puncture device.

11. The cannula device according to claim 1, wherein the connection portion and the two shielding legs are integrally formed in one piece.

* * * * *